(12) United States Patent
Jung et al.

(10) Patent No.: US 11,651,842 B2
(45) Date of Patent: May 16, 2023

(54) SERVER, PORTABLE TERMINAL DEVICE, ELECTRONIC DEVICE, AND CONTROL METHOD THEREFOR

(71) Applicant: SAMSUNG ELECTRONICS CO., LTD., Suwon-si (KR)

(72) Inventors: Hyun-joo Jung, Yongin-si (KR); Young-jae Oh, Suwon-si (KR); Seong-je Cho, Suwon-si (KR); Chul-ho Cho, Yongin-si (KR); Hyoung-seon Choi, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 627 days.

(21) Appl. No.: 16/467,670

(22) PCT Filed: Nov. 23, 2017

(86) PCT No.: PCT/KR2017/013440
§ 371 (c)(1),
(2) Date: Jun. 7, 2019

(87) PCT Pub. No.: WO2018/110854
PCT Pub. Date: Jun. 21, 2018

(65) Prior Publication Data
US 2020/0090794 A1 Mar. 19, 2020

(30) Foreign Application Priority Data
Dec. 15, 2016 (KR) .......................... 10-2016-0171638

(51) Int. Cl.
*G16H 10/60* (2018.01)
*G16H 50/30* (2018.01)
(Continued)

(52) U.S. Cl.
CPC .............. *G16H 10/60* (2018.01); *G06Q 50/22* (2013.01); *G06T 13/40* (2013.01); *G16H 40/63* (2018.01);
(Continued)

(58) Field of Classification Search
CPC ........ G16H 10/60; G16H 50/30; G16H 50/20; G16H 40/63; A63F 2300/5553; G06Q 50/22; G06T 13/40
(Continued)

(56) References Cited

U.S. PATENT DOCUMENTS 8,047,988 B2   11/2011   Lee et al.
8,612,363 B2   12/2013   Karkanias et al.
(Continued)

FOREIGN PATENT DOCUMENTS

JP   5086302       11/2012
JP   2015-115879   6/2015
(Continued)

OTHER PUBLICATIONS

International Search Report for PCT/KR2017/013440 dated Feb. 28, 2018, 4 pages with English Translation.
(Continued)

*Primary Examiner* — Mark Holcomb
(74) *Attorney, Agent, or Firm* — Nixon & Vanderhye, P.C.

(57) ABSTRACT

A server is disclosed. The server comprises: a communication interface for communicating with a user terminal device and an electronic device; a storage for storing healthcare information corresponding to an avatar of a user; and a processor for acquiring the healthcare information corresponding to the avatar of the user from the storage when information including the avatar of the user and health data is received from the user terminal device, and controlling the
(Continued)

communication interface such that guide information for guiding user behavior is transmitted to the user terminal device and/or the electronic device on the basis of the acquired healthcare information and the received health data.

2 Claims, 13 Drawing Sheets

(51) Int. Cl.
  *G16H 50/20* (2018.01)
  *G16H 40/63* (2018.01)
  *G06Q 50/22* (2018.01)
  *G06T 13/40* (2011.01)
(52) U.S. Cl.
  CPC .............. *G16H 50/20* (2018.01); *G16H 50/30* (2018.01); *A63F 2300/5553* (2013.01)
(58) Field of Classification Search
  USPC ........................................................ 705/2–4
  See application file for complete search history.

(56) References Cited

U.S. PATENT DOCUMENTS

| | | | | |
|---|---|---|---|---|
| 8,660,580 | B2* | 2/2014 | Kang | .................... H04W 4/029 455/456.3 |
| 2007/0287478 | A1 | 12/2007 | Park | |
| 2013/0183953 | A1 | 7/2013 | Park | |
| 2013/0219357 | A1* | 8/2013 | Reitan | .................... G06F 8/315 717/116 |
| 2015/0165312 | A1 | 6/2015 | Kiani | |
| 2016/0081632 | A1 | 3/2016 | Kamath et al. | |
| 2016/0086500 | A1* | 3/2016 | Kaleal, III | ............ A61B 5/165 434/257 |
| 2016/0306939 | A1* | 10/2016 | Schroeter | ........... A61B 5/02416 |
| 2017/0000388 | A1* | 1/2017 | Jessen | .................. A61B 5/0022 |

FOREIGN PATENT DOCUMENTS

| | | |
|---|---|---|
| KR | 10-2007-0005359 | 1/2007 |
| KR | 10-0750633 | 8/2007 |
| KR | 10-2012-0013530 | 2/2012 |
| KR | 10-2014-0042452 | 4/2014 |
| KR | 10-2014-0042454 | 4/2014 |
| KR | 10-1545703 | 8/2015 |
| KR | 10-2015-0117070 | 10/2015 |
| KR | 10-2016-0004436 | 1/2016 |
| KR | 10-1628713 | 6/2016 |
| KR | 10-1641676 | 7/2016 |

OTHER PUBLICATIONS

Written Opinion of the ISA for PCT/KR2017/013440 dated Feb. 28, 2018, 14 pages with English Translation.
Notice of Preliminary Rejection dated Jun. 28, 2022 in Korean Patent Application No. 10-2016-0171638 and English-language translation.

* cited by examiner

FIG. 6A
FIG. 6B
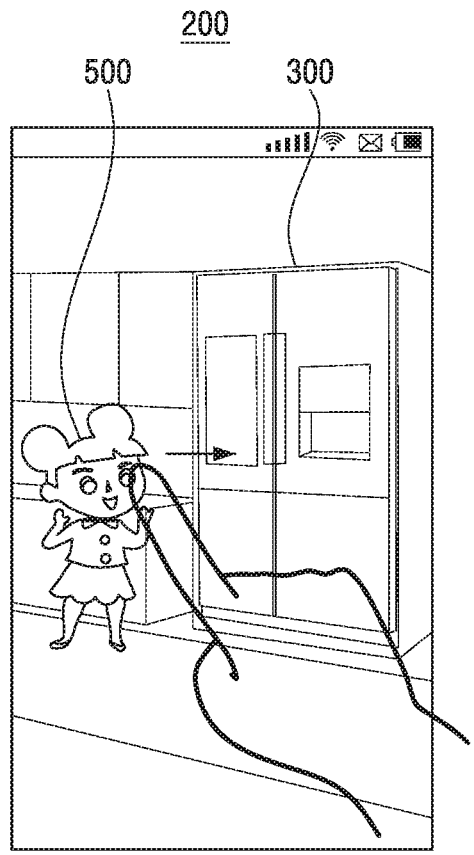
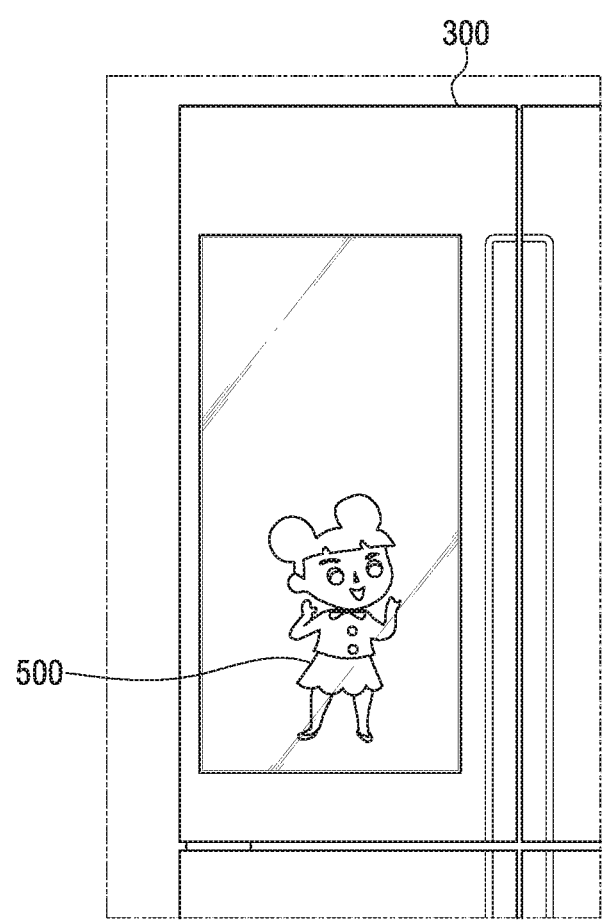

FIG. 8A
FIG. 8B
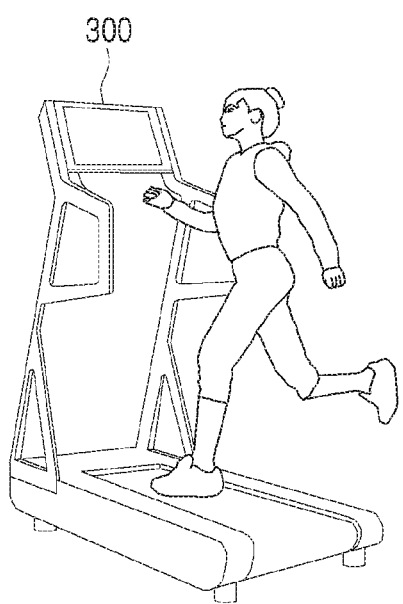
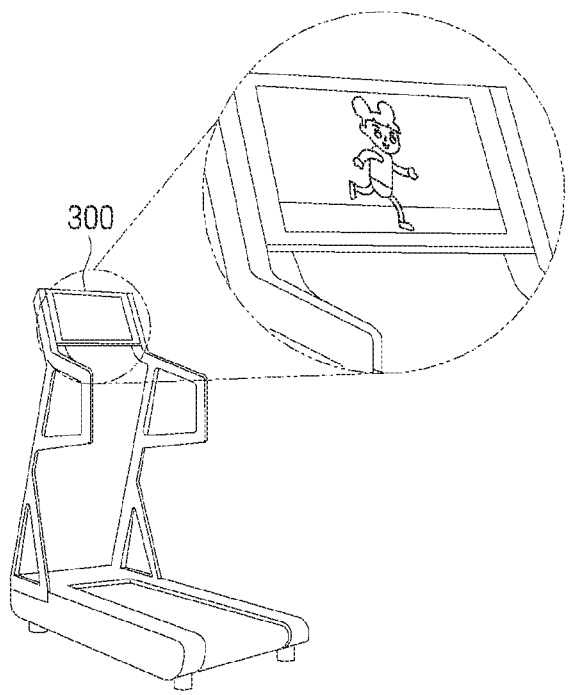

SERVER, PORTABLE TERMINAL DEVICE, ELECTRONIC DEVICE, AND CONTROL METHOD THEREFOR

This application is the U.S. national phase of International Application No. PCT/KR2017/013440 filed Nov. 23, 2017 which designated the U.S. and claims priority to KR Patent Application No. 10-2016-0171638 filed Dec. 15, 2016, the entire contents of each of which are hereby incorporated by reference.

FIELD

The disclosure relates to a server, a portable terminal device, an electronic device, and a control method therefor, and more particularly, to a server, a portable terminal device, an electronic device, and a control method therefor capable of providing guide information for health care.

DESCRIPTION OF RELATED ART

Recently, with the rapid development of electronic technology, there is an increasing interest in technology development for managing individual health in a network environment. As an example, technology for detecting and providing biometric information using a wearable device or a smart device has been developed. In addition, the detected biometric information of a user is not only stored in a user terminal but also is used to actively provide feedback on health care of the user.

Meanwhile, telemedicine which is recently and widely discussed is based on accumulated health information while living the user himself to acquire user related data. To this end, a number of personalized health care apps using wearable devices and personal terminals have been developed.

However, such a technology is difficult to interchange data between various wearable devices or storage platforms, and is not easy to secure data continuity between the devices due to the characteristics of a mobile or wearable device having a lifetime of about two to three years. In particular, when personal health care is viewed as a lifetime care over decades of life as a whole, rather than a few years of care, continuous and consecutive accumulation of personal health information is an indispensable element of personal health care. Accordingly, a method for more effectively managing a health condition of the user for a longer period of time is requested.

The disclosure provides a server, a portable terminal device, an electronic device, and a control method therefor which may provide guide information for health care using an avatar of a user and effectively manage a health of the user for a long period of time.

According to an embodiment of the disclosure, a server include: a communication interface configured to communicate with a user terminal device and an electronic device; a storage configured to store health care information corresponding to an avatar of a user; and a processor configured to obtain the health care information corresponding to the avatar of the user from the storage when information including the avatar of the user and health data is received from the user terminal device, and control the communication interface to transmit guide information for guiding a behavior of the user to at least one of the user terminal device or the electronic device based on the obtained health care information or the received health data.

The processor may transmit the guide information in the form in which the avatar guides the behavior of the user to at least one of the user terminal device or the electronic device.

When the processor receives information according to the behavior of the user from the electronic device after transmitting the guide information to at least one of the user terminal device or the electronic device, the processor may update the health care information stored in the storage based on the received information.

When it is determined that the user terminal device accesses a location of the electronic device, the processor may transmit guide information associated with a function of the electronic device.

The processor may change a state of the avatar based on the updated health care information, and transmit the changed avatar to at least one of the user terminal device or the electronic device.

The processor may change a motion of the avatar in real time based on the health data and transmit the changed motion of the avatar to at least one of the user terminal device or the electronic device.

According to another embodiment of the disclosure, a user terminal device includes: a display; a storage configured to store an avatar of a user; a communication interface configured to communicate with a server and a wearable device storing health care information corresponding to the avatar of the user; and a processor configured to display the avatar of the user according to a predetermined event, transmit the avatar of the user and health data to the server when the health data is received from the wearable device, and receive guide information for guiding a behavior of the user from the server to display the guide information through the display, wherein the guide information is information generated based on the health care information corresponding to the avatar and the health data.

The user terminal device may further include a camera, wherein the processor transmits information on a peripheral device of the user terminal device to the server, and composites and displays the avatar of the user with an image captured through the camera when guide information for guiding an access to the peripheral device is received from the server.

When the user terminal device accesses a location of the peripheral device, the processor may display the guide information in the form in which the avatar guides the behavior of the user.

When the other user terminal device of the other user is located within a predetermined distance range from the user terminal device, the processor may display an avatar of the other user together with the avatar of the user, and display guide information in the form in which the avatar of the other user guides a behavior of the avatar of the user based on the guide information.

The processor may change a motion of the avatar in real time based on the health data and display the changed motion of the avatar.

According to another embodiment of the disclosure, a method for controlling a server communicating with a user terminal device and an electronic device includes: receiving information including an avatar of a user and health data from the user terminal device; obtaining health care information corresponding to the avatar of the user; and transmitting guide information for guiding a behavior of the user to at least one of the user terminal device or the electronic device based on the obtained health care information and the received health data.

The guide information may be information in the form in which the avatar guides the behavior of the user.

The method may further include: receiving information according to the behavior of the user from the electronic device; and updating the health care information based on the received information.

The method may further include displaying guide information associated with a function of the electronic device, when it is determined that the user terminal device accesses a location of the electronic device.

The method may further include changing a state of the avatar based on the updated health care information, and transmitting the changed avatar to at least one of the user terminal device or the electronic device.

The method may further include changing a motion of the avatar in real time based on the health data, and transmitting the changed motion of the avatar to at least one of the user terminal device or the electronic device.

According to the diverse embodiments of the disclosure described above, since the guide information for guiding a user behavior using the avatar of the user may be provided and the health information of the user may be accumulated, the health condition of the user may be more effectively managed for a longer period of time.

BRIEF DESCRIPTION OF THE DRAWINGS

FIGS. 6A and 6B are diagrams for describing a method for transmitting and receiving information including an avatar and health data from the user terminal device to the electronic device according to an embodiment of the disclosure.

FIGS. 8A and 8B are diagrams for describing a process in which a motion of an avatar is changed in real time and displayed based on health data according to an embodiment of the disclosure.

DETAILED DESCRIPTION OF EXAMPLE EMBODIMENTS

First, the terms used in the specification and claims have chosen generic terms in light of the function of the disclosure. However, these terms may vary depending on the intentions of the artisan skilled in the art, legal or technical interpretation, and emergence of new technologies. In addition, some terms are arbitrarily chosen by the applicant. These terms may be construed as meaning as defined herein, and may be interpreted based on the general contents of the specification and common technical knowledge in the related art, unless otherwise defined.

Further, when it is decided that a detailed description for the known function or configuration related to the disclosure may obscure the gist of the disclosure, the detailed description thereof will be abbreviated or omitted.

Further, hereinafter, embodiments of the disclosure will be described in detail with reference to the accompanying drawings and the contents described in the accompanying drawings, but the disclosure is not limited to or limited by the embodiments.

Hereinafter, a display device according to an embodiment of the disclosure will be described with reference to the accompanying drawings.

Figure 1:
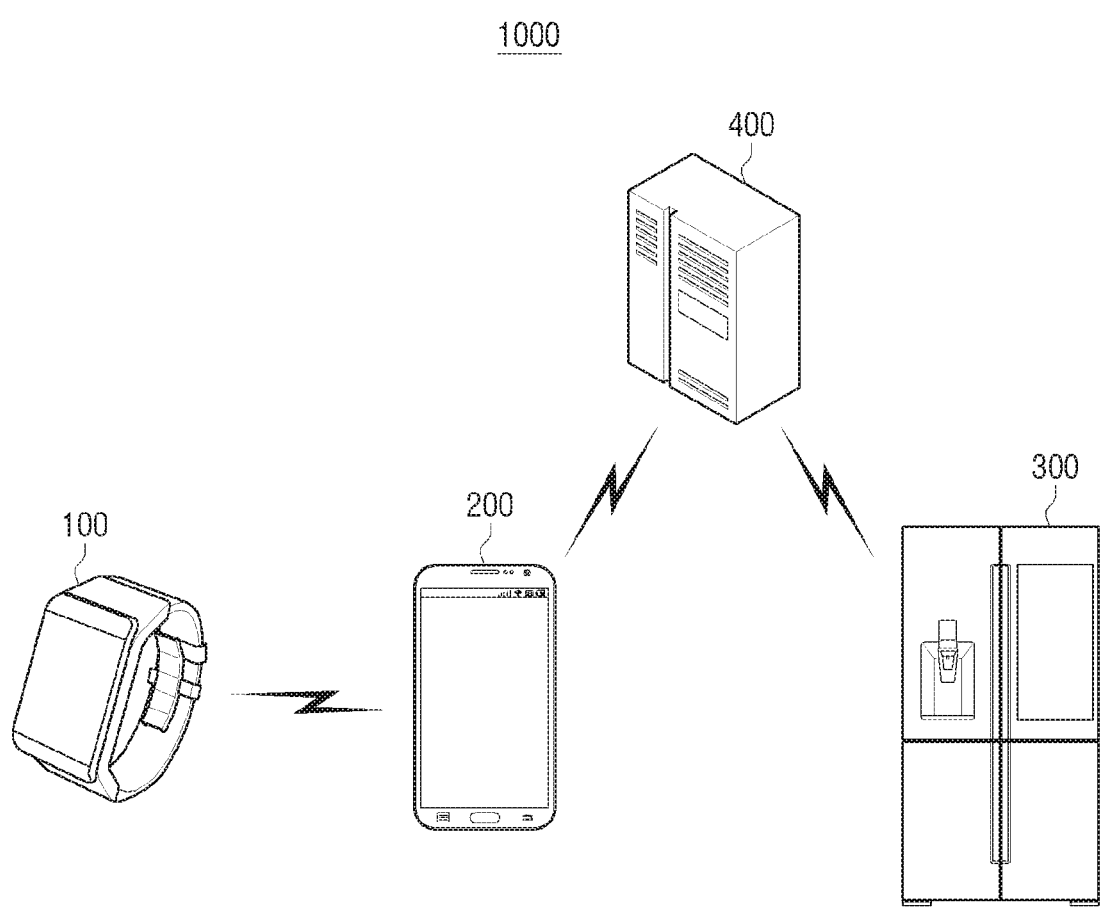
FIG. 1 is a diagram for describing a guide information providing system according to an embodiment of the disclosure.

FIG. 1 is a diagram for describing a guide information providing system according to an embodiment of the disclosure.

As illustrated in FIG. 1, a guide information providing system 1000 according to an embodiment of the disclosure may include a wearable device 100, user terminal device 200, an electronic device 300, and a server 400.

The wearable device 100 may generate health data by sensing or monitoring a bio-signal of a user.

For example, the wearable device 100 may measure blood glucose of the user. To this end, the wearable device 100 may include a continuous glucose monitoring system (cgms). Here, cgms refers to a continuous blood glucose measurement system that measures blood glucose values changing in real time by inserting a glucose sensor under a skin of a person. However, the cgms that measures the blood glucose value by an invasive method corresponds to one embodiment of the wearable device 100 and various types of sensors may be included in the wearable device 100 such as a non-invasive method, for example, a blood glucose measurement sensor in the form of a patch attached to a user's body. In addition, the wearable device 100 may measure the degree of motion, a heart rate, and the like of the user. To this end, the wearable device 100 may include an acceleration sensor, a gyro sensor, and the like. Specifically, the wearable device 100 may measure the degree of motion, the heart rate, and the like of the user using the acceleration sensor, the gyro sensor, or the like. However, this is merely one example, and the wearable device 100 may measure various health data, for example, measure body composition using human body resistance and measure sleeping information of the user using a kinect sensor.

In addition, the wearable device 100 may transmit the health data to the user terminal device 200. To this end, the wearable device 100 may include various communication chips such as a Wi-Fi chip, a Bluetooth chip, a wireless communication chip, a near field communication (NFC) chip, and the like.

Meanwhile, although FIG. 1 illustrates the wearable device 100 in the form such as a smart watch, this merely corresponds to one example. The wearable device 100 may be implemented in various types of devices capable of measuring the health data by being worn on the user's wrist, arm, waist, or ankle, such as a patch shape.

The user terminal device 200 may display an avatar of the user according to a predetermined event.

Here, the predetermined event may be an authentication procedure for identifying the user through fingerprint input, iris recognition or password input of the user. To this end, the user terminal device 200 may pre-store fingerprint data, iris data or password data of the user, and may include a scanner for fingerprint recognition of the user, a camera for iris recognition, and the like.

Thereafter, when the user authentication is completed, the user terminal device 200 may display an avatar corresponding to the authenticated user. To this end, the user terminal device 200 may store different avatars matched to each user.

In addition, when the user terminal device 200 receives the health data from the wearable device 100, the user terminal device 200 may transmit the avatar of the user and the health data to at least one of the electronic device 300 or the server 400. Here, the avatar transmitted to at least one of the electronic device 300 or the server 400 may be an image of the avatar displayed on the user terminal device 200. For example, the transmitted avatar may be the image of the avatar displayed on the user terminal device 200 according to the user authentication.

Meanwhile, here, the avatar and the health data may also be transmitted to at least one of the electronic device 300 or the server 400, but when only the avatar is transmitted, the health data may also be transmitted to at least one of the electronic device 300 or the server 400 together with the avatar. To this end, when the user terminal device 200 receives the health data from the wearable device 100, the user terminal device 200 may match the received health data to the avatar. For example, the user terminal device 200 may match the received health data to the avatar through a tag. However, a matching method is not limited to the tag, but various matching methods capable of matching data to an image may be used. When the user terminal device 200 receives a user command for transmitting the avatar, the user terminal device 200 may transmit the health data matched to the avatar together with the avatar to at least one of the electronic device 300 or the server 400. When the server 400 receives information including the avatar of the user and the health data from the user terminal device 200 or the electronic device 300, the server 400 may obtain health care information corresponding to the avatar of the user. Here, the health data may be data generated by sensing or monitoring a current bio-signal of the user in the wearable device 100, while the health care information may be health data and behavior information of the user stored in the server 400. For example, the health data stored in the server 400 may be blood glucose, body fat index, body temperature, blood pressure, and the like of the user from past to present, and the behavior information may be information on the food consumed by the user from past to present, exercise information on exercise time and kind of exercise, and the like.

To this end, the server 400 may receive and pre-store the health care information from at least one of the wearable device 100, the user terminal device 200, or the electronic device 300. Specifically, the server 400 may receive and store the health data from at least one of the wearable device 100 or the user terminal device 200, and receive and store information on the food consumed by the user and information on exercise time of the user from at least one of the user terminal device 200 or the electronic device 300.

In addition, the server 400 may divide the health care information of the user into avatars corresponding to the respective users and pre-store the health care information. That is, when the server 400 receives the information including the avatar and the health data from the user terminal device 200, the server 400 may determine whether the received avatar is an avatar of which user and may obtain the health care information of the user corresponding to the avatar among the pre-stored one or more healthcare information. In this case, the server 400 may compare the image of the avatar with a pre-stored image or compare identification information included in the avatar with pre-stored identification information to obtain the health care information of the user corresponding to the avatar of the user.

Meanwhile, here, the health care information may include biometric information and behavior information of the user. Specifically, the biometric information may be blood glucose, body fat index, body temperature, blood pressure, and the like of the user, and the behavior information may be information on the food consumed by the user and exercise information on exercise time and kind of exercise, and the like.

In addition, the server 400 may generate guide information for guiding the behavior of the user based on the obtained health care information and the received health data.

Specifically, the server 400 may feed back the obtained health care information and the received health data with each other to determine a behavior currently required for the user, and may generate the guide information for guiding the user to perform a necessary behavior at present. For example, the server 400 may feed back the obtained health care information and the received health data with each other to determine a behavior currently required for the user, and as a result of the determination, if it is determined that a blood glucose is higher than a reference value and a blood glucose level is necessary to be adjusted, the server may generate guide information for guiding the user to consume food that may reduce the blood glucose level.

Thereafter, the server 400 may transmit the guide information to at least one of the user terminal device 200 or the electronic device 300.

Meanwhile, the server 400 may be implemented as a central server (or an integrated server) for taking charge of interaction between various operating systems and applications in a network system, or a cloud server using cloud computing technology. Here, cloud computing means Internet-based computing technology, and is a Web-based software service that puts a program on a utility data server on the Internet and then loads and uses the program into a computer or cell phone whenever the program is needed.

Meanwhile, according to another embodiment of the disclosure, the wearable device 100 may receive the guide information by communicating with the server 400, and may display the guide information. Specifically, the wearable device 100 may further include a display (not shown), a communication interface (not shown) communicating with the server, a storage (not shown) storing the avatar of the user, a sensor for user authentication, and the like. Accordingly, the wearable device 100 (e.g., the smart watch) may transmit the health data of the user to the server 400, and may display the guide information received from the server 400. Thereby, even in a state in which the user does not have the user terminal device 200, the user may be provided with the guide information including the avatar through the wearable device 100, thereby more effectively managing the health.

Hereinafter, a method for generating and providing guide information will be described in more detail with the drawings.

Figure 2:
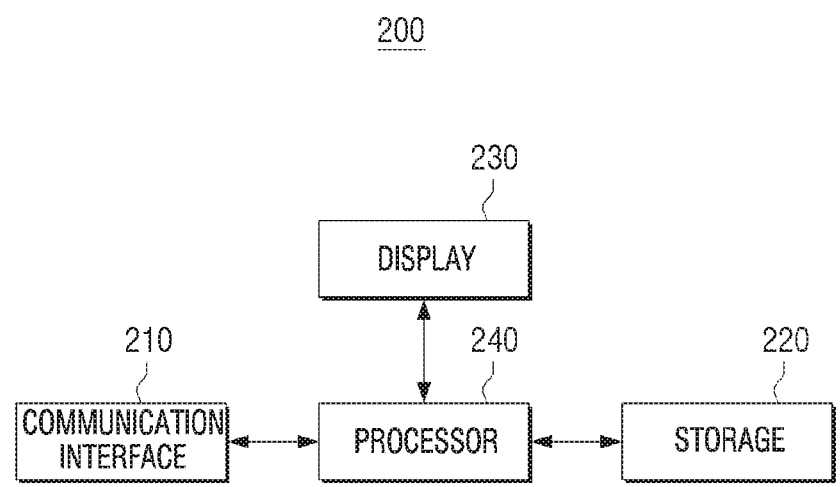
FIG. 2 is a block diagram for describing a user terminal device according to an embodiment of the disclosure.

FIG. 2 is a block diagram for describing a user terminal device according to an embodiment of the disclosure.

Referring to FIG. 2, the user terminal apparatus 200 may include a communication interface 210, a storage 220, a display 230, and a processor 240. Here, the user terminal device 200 may be implemented as various electronic devices such as a tablet PC, a digital camera, a camcorder, a notebook PC, a desktop, a PDA, an MP3, and the like having a display including a mobile phone and capable of communicating with an external device.

The communication interface 210 may perform communication with various types of external devices according to various types of communication schemes.

In particular, the communication interface 210 may communicate with the wearable device 100, the electronic device 300, and the server 400. Specifically, the communication interface 210 may communicate with the wearable device 100 to receive the health data, and may communicate with the electronic device 300 or the server 400 to transmit the health data and the avatar to at least one of the electronic device 300 or the server 400.

To this end, the communication interface 210 may include various communication chips such as a Wi-Fi chip, a Bluetooth chip, a wireless communication chip, a near field communication (NFC) chip, and the like. Here, the Wi-Fi chip and the Bluetooth chip perform communication in a Wi-Fi scheme and a Bluetooth scheme, respectively. In case of using the Wi-Fi chip or the Bluetooth chip, various connection information such as a service set identifier (SSID), a session key, and the like, is first transmitted and received, communication is connected using the connection information, and various information may then be transmitted and received. The wireless communication chip means a chip performing communication depending on various communication protocols such as Institute of Electrical and Electronics Engineers (IEEE), Zigbee, $3^{rd}$ generation (3G), $3^{rd}$ generation partnership project (3GPP), long term evolution (LTE), and the like. The NFC chip means a chip operating in an NFC scheme using a band of 13.56 MHz among various radio frequency identification (RFID) frequency bands such as 135 kHz, 13.56 MHz, 433 MHz, 860 to 960 MHz, 2.45 GHz, and the like.

The storage 220 may store various programs and data required for an operation of the user terminal device 200. In particular, the storage 220 may store user identification information and avatars.

In this case, the storage 220 may divide and store the avatars corresponding to the user identification information for each user. Here, the user identification information may be information on the fingerprint, iris, and password of the user.

In addition, the storage 220 may store the health data received from the wearable device 100.

To this end, the storage 220 may be implemented as a variety of storage media, such as a hard disk, a non-volatile memory, a volatile memory, and the like.

Meanwhile, the storage 220 may store an operating system (OS) for controlling a general operation of the components of the user terminal device 200, and commands or data associated with the components of the user terminal device 200. Accordingly, the processor 240 may perform a booting of the operating system to control a number of hardware or software components connected to the processor 240, may load and process commands or data received from at least one of other components in the volatile memory, and may store various data in the non-volatile memory.

The display 230 may display various screens.

For example, the display 230 may display the guide information received from the server 400. To this end, the display 230 may be implemented as a liquid crystal display (LCD), an organic light emitting diode (OLED) display, or the like. Meanwhile, details related to the guide information will be described later.

The processor 240 controls a general operation of the user terminal device 200. To this end, the processor 240 may include a central processing unit (CPU), a random access memory (RAM), and a read only memory (ROM), and may execute operations or data processing relating to control of other components included in the user terminal device 200.

First, when the processor 240 is connected to the wearable device 100 through the communication interface 210, the processor 240 may control the communication interface 210 to transmit a transmission request command for the health data to the wearable device 100. Meanwhile, when the processor 240 is connected to the wearable device 100 through the communication interface 210 without separately transmitting the transmission request command for the health data to the wearable device 100, the processor 240 may control the communication interface 210 to automatically receive the health data from the wearable device 100.

In this case, the wearable device 100 may transmit information on the health data of the user to the user terminal device 200, and the processor 240 may store the health data received from the wearable device 100 in the storage 220. Here, the processor 240 may not only automatically store the health data received from the wearable device 100 in the storage 200, but may also store the health data in a predetermined manner according to a user operation. For example, if there is a user setting related to whether or not the received health data is stored or related to a storage period, the processor 240 may store the received health data through an additional user input, or the like.

In addition, when a predetermined event occurs, the processor 240 may control the display 230 to display the avatar of the user. Meanwhile, the predetermined event herein may be an authentication procedure for identifying the user as described above. For example, when the user inputs a fingerprint to the fingerprint scanner of the user terminal device 200, allows a camera to recognize the iris, or inputs the password, the processor 240 may determine whether the user is an authenticated user, and control the display 230 to display an avatar corresponding to the authenticated user when it is determined that the user is the authenticated user.

In addition, the processor 240 may control the communication interface 210 to transmit the displayed avatar and the health data received from the wearable device 100 to at least one of the electronic device 300 or the server 400. Meanwhile, here, the avatar and the health data may also be transmitted to at least one of the electronic device 300 or the server 400, but when only the avatar is transmitted to the server 400, the health data may also be transmitted to at least one of the electronic device 300 or the server 400 together with the avatar in a state mapping to the avatar.

Thereafter, the processor 240 may control the communication interface 210 to receive the guide information from the server 400. Here, the guide information may be guide information for guiding a behavior of the user. Meanwhile, details related to the guide information will be described later.

Meanwhile, the user terminal device 200 may further include various components in addition to the components described with reference to FIG. 2.

In particular, the user terminal device 200 may further include a camera. Here, the camera is a component for capturing a still image or a moving image according to a control of the user, and may be implemented as a plurality of cameras such as a front camera and a rear camera.

In addition, the user terminal device 200 may display the guide information by compositing the avatar with the image photographed through the camera. Specifically, the guide information may be provided using augmented reality technology.

Here, unlike virtual reality technology, the augmented reality technology refers to technology of overlapping and displaying AR contents on an image really photographed through a special interface based on real-time processing.

In this case, if it is determined that the user terminal device 200 accesses a specific location, the processor 240 may provide the AR contents including the guiding information by compositing the avatar with the photographed image.

Alternatively, the processor 240 may transmit the photographed image to the server 400 together with location information of the user terminal device 200, and may receive and provide the AR contents from the server 400. To this end, the user terminal device 200 may further include a location sensor for sensing a location of the user terminal device 200, and an AR content-image matching device for matching the images captured in real time and the AR contents provided from the server 400, in addition to the camera for capturing the images.

Figure 3:
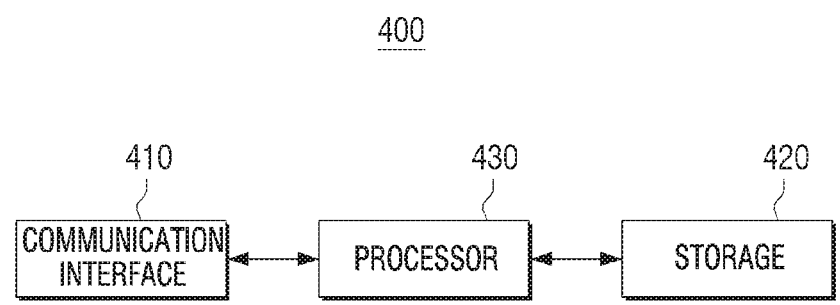
FIG. 3 is a block diagram for describing a server according to an embodiment of the disclosure.

FIG. 3 is a block diagram for describing a server according to an embodiment of the disclosure.

Referring to FIG. 3, the server 400 may include a communication interface 410, a storage 420, and a processor 430. The server 400 may be implemented in various forms such as an external server of the user terminal device 200, an embedded server embedded in the user terminal device 200, an embedded chip embedded in the user terminal device 200, and the like.

The communication interface 410 may perform communication with various types of external devices according to various types of communication schemes.

In particular, the communication interface 410 may perform communication with the user terminal device 200 and the electronic device 300. Specifically, the communication interface 410 may receive the information including the avatar and the health data from the user terminal device 200 or the electronic device 300, and may transmit the generated guide information to at least one of the user terminal device 200 or the electronic device 300.

To this end, the communication interface 410 may include various communication chips. Here, the Wi-Fi chip and the Bluetooth chip perform communication in a Wi-Hi scheme and a Bluetooth scheme, respectively. In case of using the Wi-Fi chip or the Bluetooth chip, various connection information such as a service set identifier (SSID), a session key, and the like, is first transmitted and received, communication is connected using the connection information, and various information may then be transmitted and received. The wireless communication chip means a chip performing communication depending on various communication protocols such as Institute of Electrical and Electronics Engineers (IEEE), Zigbee, $3^{rd}$ generation (3G), $3^{rd}$ generation partnership project (3GPP), long term evolution (LTE), and the like. The NFC chip means a chip operating in an NFC scheme using a band of 13.56 MHz among various radio frequency identification (RFID) frequency bands such as 135 kHz, 13.56 MHz, 433 MHz, 860 to 960 MHz, 2.45 GHz, and the like.

The storage 420 may store various programs and data required for an operation of the server 400. In particular, the storage 420 may divide and store the health care information corresponding to the avatar of the user for each avatar. For example, the storage 420 may map and store first health care information corresponding to a first user to a first avatar, and may map and store second health care information corresponding to a second user to a second avatar.

To this end, the storage 420 may be implemented as a variety of storage media, such as a hard disk, a non-volatile memory, a volatile memory, and the like.

Meanwhile, the storage 420 may store an operating system (OS) for controlling a general operation of the components of the server 400, and commands or data associated with the user terminal device 300 and the electronic device 300. Accordingly, the processor 430 may perform a booting of the operating system to control a number of hardware or software components connected to the processor 430, may load and process commands or data received from at least one of other components in the volatile memory, and may store various data in the non-volatile memory.

The processor 430 controls a general operation of the server 400. To this end, the processor 430 may include a central processing unit (CPU), a random access memory (RAM), and a read only memory (ROM), and may execute operations or data processing relating to control of other components included in the server 400.

First, if the processor 430 is connected to at least one of the user terminal device 200 or the electronic device 300 through the communication interface 410, the processor 430 may control the communication interface 410 to receive the information including the avatar of the user and the health data from at least one of the user terminal device 200 or the electronic device 300.

In this case, the communication interface 410 may receive the information including the avatar of the user and the health data from at least one of the user terminal device 200 or the electronic device 300, and the processor 430 may store the information including the avatar of the user and the health data received from at least one of the user terminal device 200 or the electronic device 300 in the storage 420.

In addition, the processor 430 may obtain health care information corresponding to the avatar of the user from at least one health care information stored in the storage 420. Specifically, the processor 130 may obtain the health care information corresponding to the avatar received from at least one of the user terminal device 200 or the electronic device 300 from the health care information divided and stored for each avatar.

Here, the health care information corresponding to the avatar may include biometric information, behavior information, and the like associated with the user corresponding to the avatar. For example, the health care information may include biometric information such as blood glucose, body fat index, body temperature, blood pressure, and the like of the user, information on the food consumed by the user, exercise information on exercise time and kind of exercise, and the like.

Thereafter, the processor 430 may generate guide information for guiding the behavior of the user based on the obtained health care information and the received health data.

Specifically, the processor 430 may determine a behavior which is currently required for the user based on the obtained health care information and the received health data. For example, as a result obtained by analyzing the obtained health care information and the received health care data, if it is determined that a blood glucose level is higher than a reference value, the processor 430 may determine that the user needs to currently consume food for controlling the blood glucose level. Accordingly, the processor 430 may generate guide information for guiding the user to consume the food required for blood glucose level control.

Here, the guide information may be information in which the avatar guides the behavior of the user.

For example, if it is determined that the user needs to currently consume the food for controlling the blood glucose level, the processor 430 may use an avatar to generate guide information including a message that the avatar wants to eat a green tea. As another example, if it is determined that a current body fat index of the user is higher than a reference value, the processor 430 may use an avatar to generate guide information including a message that the avatar wants to run. In this case, the message may be a form that the avatar speaks, and the shape of the avatar may also be modified according to the message of the avatar. For example, the guide information including the message that the avatar wants to run may include an avatar of a running shape.

Thereafter, the processor 430 may control the communication interface 410 to transmit the generated guide information to at least one of the user terminal device 200 or the electronic device 400.

Accordingly, the user terminal device 200 or the electronic device 400 may display the received guide information through the display.

Meanwhile, if the process 430 receives information according to the behavior of the user from at least one of the user terminal device 200 or the electronic device 400 after transmitting the generated guide information to at least one of the user terminal device 200 or the electronic device 400, the processor 430 may update the health care information stored in the storage based on the received information.

For example, if the processor 430 receives information that the user drank the green tea from at least one of the user terminal device 200 or the electronic device 400 after transmitting guide information for recommending the green tea for blood glucose control, the processor 430 may update the health care information stored in the storage based on the information that the user drank the green tea.

Here, the information according to the behavior of the user may be transmitted to the server 400 according to a user operation performed in the user terminal device 200 or the electronic device 300. Specifically, if the user inputs to the user terminal device 200 or the electronic device 300 that the user has performed a specific behavior, input user behavior information may be transmitted to the server 400. For example, if the user directly inputs information that the user has drank the green tea to the user terminal 200 to transmit the information to the server 400 through the communication interface 210 or touches the green tea displayed on the electronic device 300, the electronic device 300 may transmit the information that the user has drank the green tea to the server 400 through a communication interface (not shown).

In addition, the processor 430 may change a state of the avatar based on the updated health care information, and transmit the changed avatar to at least one of the user terminal device or the electronic device.

For example, if it is determined that the current blood glucose level of the user is higher than the reference value based on the health care information and the health data, the processor 430 may transmit guide information including a crying avatar to at least one of the user terminal device or the electronic device, and if it is determined that the blood glucose level of the user is returned to a normal value based on the health care information updated according to the behavior of the user after transmitting the guide information, the processor 430 may transmit guide information including a smiling avatar.

However, according to another embodiment, the user terminal device 200 and the electronic device 300 may store various forms of avatar information and guide messages, and in this case, it is also possible to provide guide information including the pre-stored avatar and guide message in accordance with the control signal of the server 400.

In addition, if it is determined that the user terminal device 200 accesses the location of the electronic device 300, the processor 430 may transmit guide information associated with the function of the electronic device 300.

Here, the information associated with the function of the electronic device 300 may vary depending on the type of electronic device. For example, if it is determined that the electronic device 300 is a refrigerator, the processor 430 may transmit guide information including information on food to be currently consumed by the user, and if it is determined that the electronic device 300 is a running machine, the processor 430 may transmit guide information including information on calories to be currently consumed by the user.

To this end, the processor 430 may receive information on locations of the user terminal device 200 and the electronic device 300 from the user terminal device 200. Specifically, the user terminal device 200 and the electronic device 300 may receive a GPS signal including information on the location from a satellite using a GPS chip and transmit, the received GPS signal to the server 400. Accordingly, the processor 430 may receive the information on the locations of the user terminal device 200 and the electronic device 300, and if it is determined that the user terminal device 200 accesses the location of the electronic device 300, the processor 430 may transmit the guide information associated with the function of the electronic device 300.

In addition, the processor 430 may determine whether the user terminal device 200 accesses the location of the electronic device 300 using a beacon, which is a Bluetooth protocol based near field communication device. Specifically, the user terminal device 100 may receive a beacon signal from the beacon attached to the electronic device 300 and then transmit the beacon signal to the server 400, and accordingly, the processor 430 may determine that the user terminal device 100 accesses the electronic device 200. In addition, the processor 430 may determine whether the user terminal device 200 accesses the location of the electronic device 300 using an NFC scheme. Specifically, the user terminal device 100 may tag the electronic device 300 on which an NFC tag is mounted and then transmit the tagged information to the server 400, and accordingly, the processor 430 may determined that the user terminal device 100 accesses the electronic device 200.

However, this is merely one example, and the user terminal device 200 and the electronic device 300 may transmit the location information of the user terminal device 200 or the electronic device 300 to the server 400 using various schemes such as Wi-Fi and CDMA in addition to GPS, the beacon, and the NFC scheme.

Meanwhile, the user terminal device 100 may also pre-store the location information of the electronic device 300. For example, the user terminal device 100 may coordinate and store the location of the electronic device 200 in the home where the user resides. Here, the location of the electronic device 200 may be gps coordinates including latitude and longitude. Accordingly, the processor 430 may determine whether or not the user terminal device 100 accesses the electronic device 200 using the location information received from the user terminal device 100 and a location coordinate of the electronic device 200. In this case, even though a network module is not mounted in the electronic device 200 itself, there is an effect that the server 400 may determine whether the user terminal 100 and the electronic device 200 are close to each other.

Meanwhile, the processor 430 may pre-store the information on the location of the electronic device 300 in the storage 420. For example, in case that a communication module is not mounted in the electronic device 300, the processor 430 may pre-store the location of the electronic device 300 by the user input in that the processor 430 may not receive the information on the location of the electronic device 300 from the electronic device 300. Accordingly, the processor 430 may also determine whether the user terminal device 200 accesses the location of the electronic device 300 using the pre-stored information on the location of the electronic device 300.

In addition, the processor 430 may change a motion of the avatar in real time based on the health data to transmit the changed motion to at least one of the user terminal device or the electronic device.

Specifically, the processor 430 may detect the degree of blood glucose level control and the degree of heart rate fluctuation of the user based on the health data received from the user terminal device 200 or the electronic device 300, and accordingly, the processor 430 may recognize the behavior of the user and change the motion of the avatar in real time so as to correspond to a motion of the user to transmit the changed motion to at least one of the user terminal device or the electronic device.

For example, if the processor 430 receives health data including motion information speed information of the user, the processor 430 may recognize that the user is running and may transmit a form that is the motion that the avatar runs to correspond to the running user, and if the processor 430 receives health data including motion information or turn over information of the user, the processor 430 may recognize that the user is sleeping and may transmit a form that is the motion that the avatar sleeps on to correspond to the sleeping user.

Meanwhile, if it is determined that an avatar of the other user is an avatar who has access to the avatar of the user, the processor 430 may transmit the health care information to a user terminal device of the other user.

To this end, the server 400 may be pre-stored with the access to the health care information of the avatar 820 of the user by another user. For example, the server 400 may be stored with the access to health care information of a second avatar by a first avatar. Accordingly, if the received avatar corresponds to the first user, the server 400 may transmit the health care information of the second user to the terminal device of the first user.

Accordingly, if the user corresponding to the second avatar is a child and the user corresponding to the first avatar is a guardian, the guardian may manage the health of the child more efficiently in that the health care information may be managed by the guardian in real time.

Meanwhile, the server 400 may further include various components in addition to the components described with reference to FIG. 3.

In particular, the server 400 may further include components for implementing augmented reality technology. Specifically, the server 400 may further include a location determiner for calculating the location of the user terminal device 200 using the location information received from the user terminal device 200, an AR content generator for extracting the content corresponding to the calculated location and converting the extracted content into a format compatible with augmented reality, and a communicator for transmitting the generated AR content to the user terminal device 200.

Accordingly, the server 400 may extract content corresponding to the image according to the image provided from the user terminal device 200 and the location of the user terminal device 200, and convert the extracted content into the AR content to provide the AR content to the user terminal device 200.

Hereinafter, embodiments of the disclosure will be described in more detail with reference to the drawings. Meanwhile, the description of the parts overlapping with those described above will be omitted.

Figure 4:
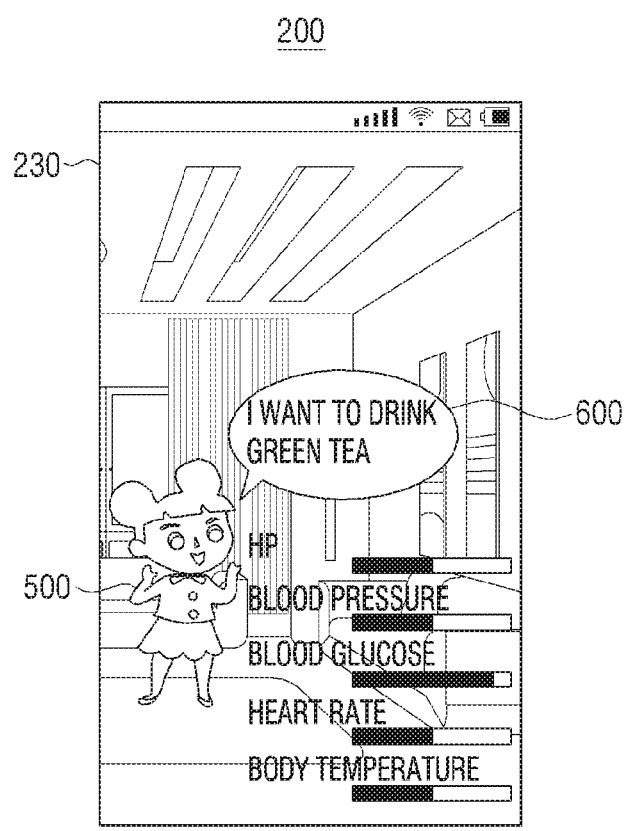
FIG. 4 is a diagram for describing guide information displayed on the user terminal device according to an embodiment of the disclosure.

FIG. 4 is a diagram for describing guide information displayed on the user terminal device according to an embodiment of the disclosure.

Referring to FIG. 4, the guide information for guiding the behavior of the user may be displayed on the display 230 of the user terminal device 200.

To this end, if the server 400 receives the information including an avatar 500 of the user and health data from the user terminal device 200, the server 400 may obtain health care information corresponding to the avatar 500 of the user among pre-stored health care information, and may determine a current health condition of the user based on the obtained health care information and the received health data. Specifically, the server 400 may determine the current health condition of the user by feeding back the biometric information of the user stored in the obtained health care information or current biometric information of the user.

In addition, the server 400 may determine behavior currently required for the user based on the current health condition of the user. For example, if it is determined that a current blood glucose level of the user exceeds a reference value, the server 400 may determine that the user needs to consume food for blood glucose level control, and if it is determined that a current fat body index of the user exceeds a reference value, the server 400 may determine that exercise for controlling body fat is necessary.

Thereafter, the server 400 may provide guide information including information for guiding the user to actually perform the behavior determined to be required for the user. For example, as illustrated in FIG. 4, if it is determined that the blood glucose level of the user exceeds the reference value and the user needs to consume a green tea to control the blood glucose level, the server 400 may transmit guide information including the avatar 500 of the user and a message 600 that the user wants to eat the green tea to the user terminal device 200. In some cases, it is also possible to transmit only guide information including only the message 600 that the user wants to eat the green tea to the user terminal device 200.

Meanwhile, as illustrated in FIG. 4, the guide information may include information on the current health condition of the user, for example, information on physical strength (HP), blood pressure, blood glucose, heart rate, and body temperature. Here, the physical strength (HP) of the user may be generated based on the sleep time and the health care information measured using the Kinect sensor included in the wearable device 100, that is, the health data and the behavior information of the user stored in the server 400. Specifically, the server 400 may determine the sleep time of the user, whether or not the user consumes healthy foods, or the like by feeding back the health data and the health care information to each other, and may generate the physical strength (HP) of the user included in the guide information differently based the on determination. Meanwhile, the blood pressure may be generated based on blood pressure measured by a blood pressure measuring sensor included in the wearable device 100. Here, the blood pressure measuring sensor may be a sensor that may measure the blood pressure of the user in real time such as an infrared sensor capable of calculating arterial mean blood pressure by measuring photo plethysmography (PPG) of a finger or wrist, an infrared sensor capable of calculating the blood pressure by calculating electrocardiogram (EGG) and the pulse wave of the user and calculating a pulse wave transmission time, or the like. In addition, the body temperature may be generated based on a temperature measured by a temperature measurement sensor included in the wearable device 100. Meanwhile, because method of generating information on blood glucose and heart rate has been described above, it will be omitted here.

Accordingly, the user may visually determine own current health condition state and feel the necessity to act according to the guide information, so that own health may be managed more efficiently.

Figure 5A:
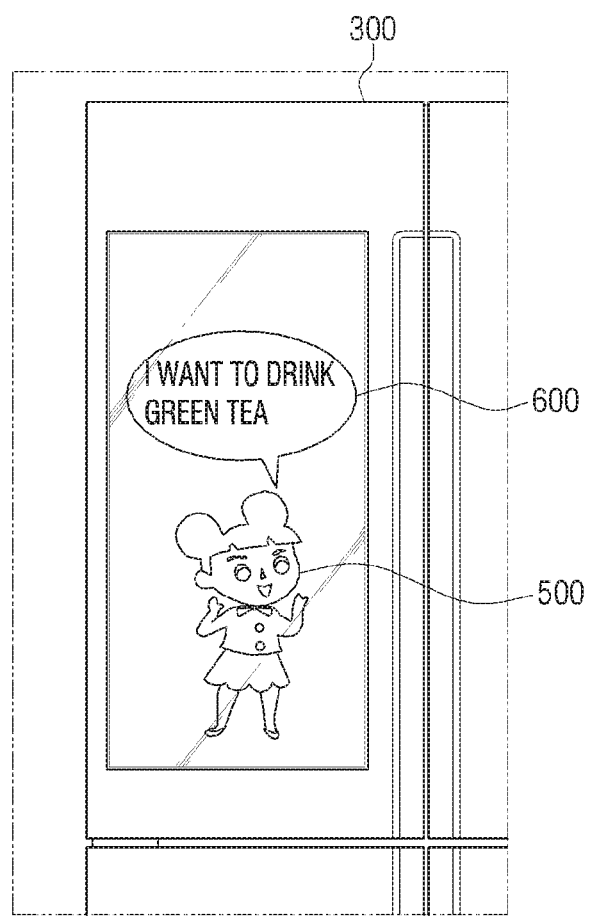
FIGS. 5A and 5B are diagrams for describing guide information displayed on the electronic device according to an embodiment of the disclosure.
Figure 5B:
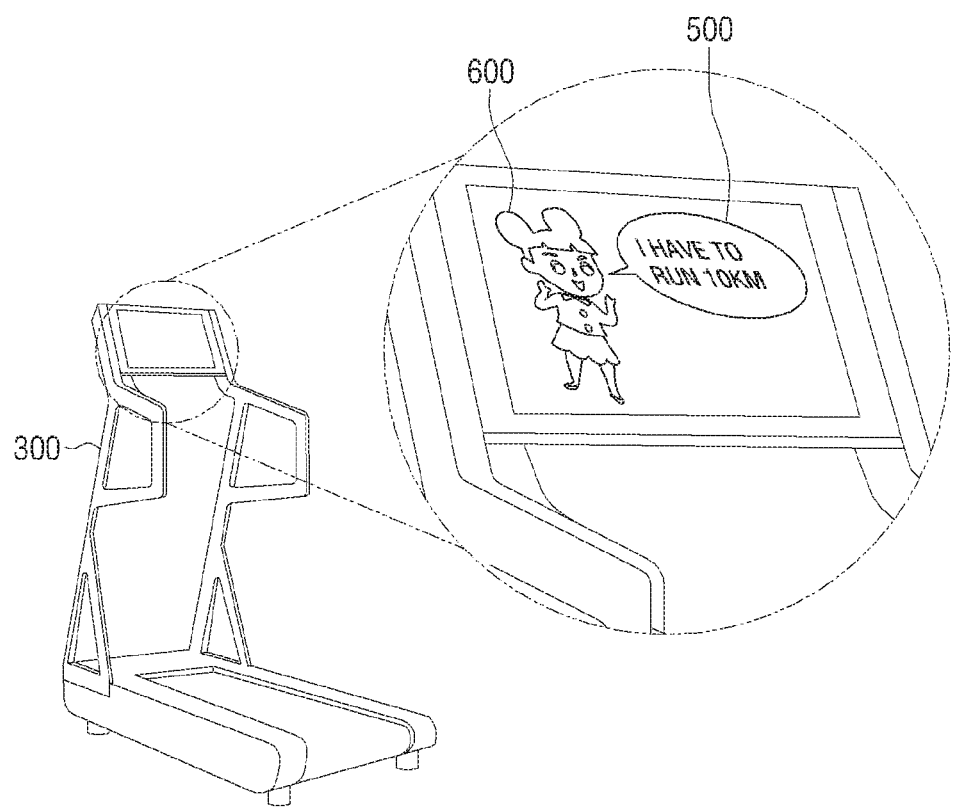

FIGS. 5A and 5B are diagrams for describing guide information displayed on the electronic device according to an embodiment of the disclosure.

Referring to FIGS. 5A and 5B, the guide information for guiding the behavior of the user may be displayed on the display 230 of the electronic device 300.

To this end, if the server 400 receives the information including the avatar 500 of the user and the health data from the electronic device 300, the server 400 may obtain health care information corresponding to the avatar 500 of the user, and may determine a current health condition of the user based on the obtained health care information and the received health data. Specifically, the server 400 may determine the current health condition of the user by feeding back the biometric information of the user stored in the obtained health care information or current biometric information of the user.

In addition, the server 400 may determine a behavior currently required for the user based on the health condition of the user and may provide guide information including information for guiding the user to actually perform the determined behavior.

For example, referring to FIG. 5A, if it is determined that the blood glucose level of the user exceeds the reference value and the user needs to consume a green tea to control the blood glucose level, the server 400 may transmit guide information including the avatar 500 of the user and a message 600 that the user wants to eat the green tea to the electronic device 300.

In addition, referring to FIG. 5B, if it is determined that the fat body index of the user exceeds the reference value and exercise for controlling body fat necessary, the server 400 may transmit guide information including the avatar 500 of the user and a message 600 that the exercise is necessary to the electronic device 300.

Accordingly, the electronic device 200 may display the received guide information to guide the user to drink the green tea according to the guide information.

Meanwhile, the guide information may be guide information associated with the function of the electronic device 300.

For example, the server 400 may determine that both food consumption and exercise are necessary based on the health condition of the user. In this case, if it is determined that the user accesses a location of the refrigerator, the server 400 may transmit guide information associated with a function of the refrigerator to the electronic device 300 as illustrated in FIG. 5A, and if it is determined that the user accesses a running machine, the server 400 may transmits guide information associated with a function of the running machine to the electronic device 300 as illustrated in FIG. 5B.

Meanwhile, the server 400 may determine a location of the user based on the location of the user terminal device 200. Here, the location of the user terminal device 200 may be sensed by the GPS signal or the like, and the detailed description associated with the location information has been described above.

Accordingly, the user may be provided with the guide information associated with the function of the accessed electronic device 300, and may thus manage more efficiently the health in that the user may immediately perform the necessary behavior.

FIGS. 6A and 6B are diagrams for describing a method for transmitting information including an avatar and health data from the user terminal device 200 to the electronic device 400 according to an embodiment of the disclosure.

First, as illustrated in FIG. 6A, the avatar 500 corresponding to the user may be displayed on the user terminal device 200.

In this case, the user performs an operation of touching the avatar 500 and then pushing the avatar 500, i.e., a swipe operation, the user terminal device 200 may communicate with the electronic device 300 to transmit the avatar 500 to the electronic device 300. Specifically, in state in which the communication between the user terminal device 200 and the electronic device 300 is connected through the user input, the user terminal device 200 may be preset to transmit the touched avatar to the electronic device 300 when the swipe operation of the user is sensed.

Meanwhile, if it is determined that the user accesses the location of the electronic device 300, the user terminal device 200 may automatically connect the communication with the electronic device 300. Here, the user terminal device 200 and the electronic device 300 may be connected to each other through the Internet of Things (IoT) based network. For example, if the user terminal device 200 exists within a predetermined distance range from the electronic device 300, the electronic device 300 may transmit a sensing signal to the IoT management server (not shown). In addition, if the IoT management server (not shown) transmits the sensing signal to the user terminal device 200, the user terminal device 200 may be preset to perform the communication connection with the electronic device 300.

Meanwhile, the avatar transmitted from the user terminal device 200 to the electronic device 300 may include information on the health data. Specifically, by mapping the health data to the avatar displayed on the user terminal device 200, the avatar may include the information on the health data. Accordingly, the electronic device 300 may receive the avatar including the information on the health data and transmit the avatar to the server 400, thereby receiving the guide information based on the health data.

Thereafter, the electronic device 300 may directly receive the guide information from the server 400 and display the guide information.

Accordingly, the user may immediately perform a current necessary behavior in that the user may be provided with the guide information through the display of the electronic device 300, and may thus manage more efficiently the health.

Meanwhile, although FIGS. 6A and 6B describe that the avatar may be transmitted to the electronic device through the swipe operation, the avatar may be transmitted to the electronic device 300 by various methods such as an operation of touching the avatar, an operation of shaking the user terminal device 200, and the like.

Figure 7A:
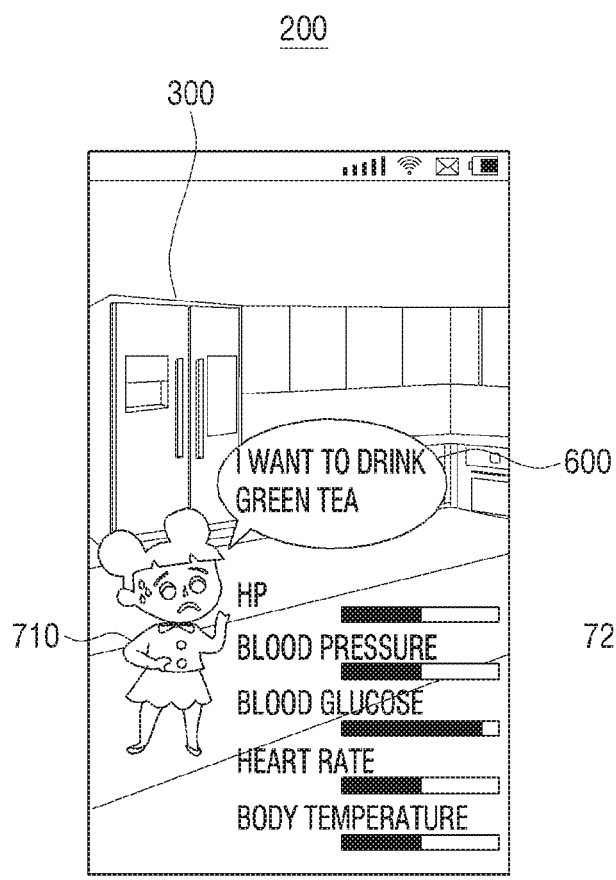
FIGS. 7A and 7B are diagrams for describing guide information to be displayed by changing a state of an avatar based on updated healthcare information according to an embodiment of the disclosure.
Figure 7B:
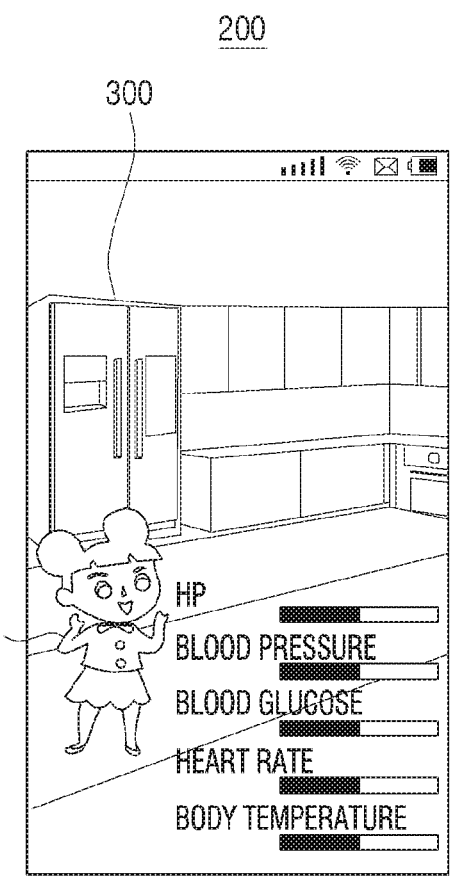

FIGS. 7A and 7B are diagrams for describing guide information to be displayed by changing a state of an avatar based on updated healthcare information according to an embodiment of the disclosure.

Referring to FIG. 7A, if it is determined that the current blood glucose level of the user is higher than the reference value based on the health care information and the health data, the server 400 may generate guide information including a sick avatar 710 and transmit the guide information to the portable terminal device 200.

Thereafter, if the information according to the behavior of the user is received from the electronic device 300, the server 400 may update the health care information based on the received information. For example, if the information according to the behavior of the user is information that the user has drank the green tea according to the guide information, the server 400 may update and store the information that the user has drank the green tea in the health care information.

In addition, if it is determined that the blood glucose level of the user is controlled to an appropriate value based on the updated healthcare information and the health data received from the wearable device 100, the server 400 may transmit guide information including a smiling avatar 720 to the user terminal device 200 by changing the sick avatar 710, as illustrated in FIG. 7B. Specifically, the wearable device 100 may generates the health data by measuring a bio-signal of the user in real time, and the server 400 may receive the health data generated in the wearable device 100 in real time. Accordingly, the server 400 may receive the health data reflecting the behavior or the user, for example, the updated health data in which the blood glucose level is reduced when the user perform the behavior of drinking the green tea, and the server 400 may change the shape of the avatar based on the updated health data and the updated health care information described above and display the changed avatar. Meanwhile, because a method for receiving the information according to the behavior of the user is described above, a description thereof will be omitted herein.

Accordingly, the user may more efficiently manage own health in that the user may confirm own health condition in real time through the avatar changed based on the updated health care information.

FIGS. 8A and 8B are diagrams for describing a process in which a motion of an avatar is changed in real time and displayed based on health data according to an embodiment of the disclosure.

As illustrated in FIG. 8A, the user may be running using the electronic device 300, for example, the running machine. In this case, the wearable device 100 may measure a degree of motion, heart rate, and the like of the user using an acceleration sensor, a gyro sensor, or the like, and if the health data including the heart rate of the user is received from the wearable device 100 or the user terminal device 200, the server 400 may analyze the health data and determine that the user running. Accordingly, as illustrated in FIG. 8B, the server 100 may generate a running avatar to correspond to the running user and transmit the generated avatar to the electronic device 300. Accordingly, the user may perform an exercise in an interesting manner while watching a real time changed shape of the avatar.

Figures 9A, 9B:
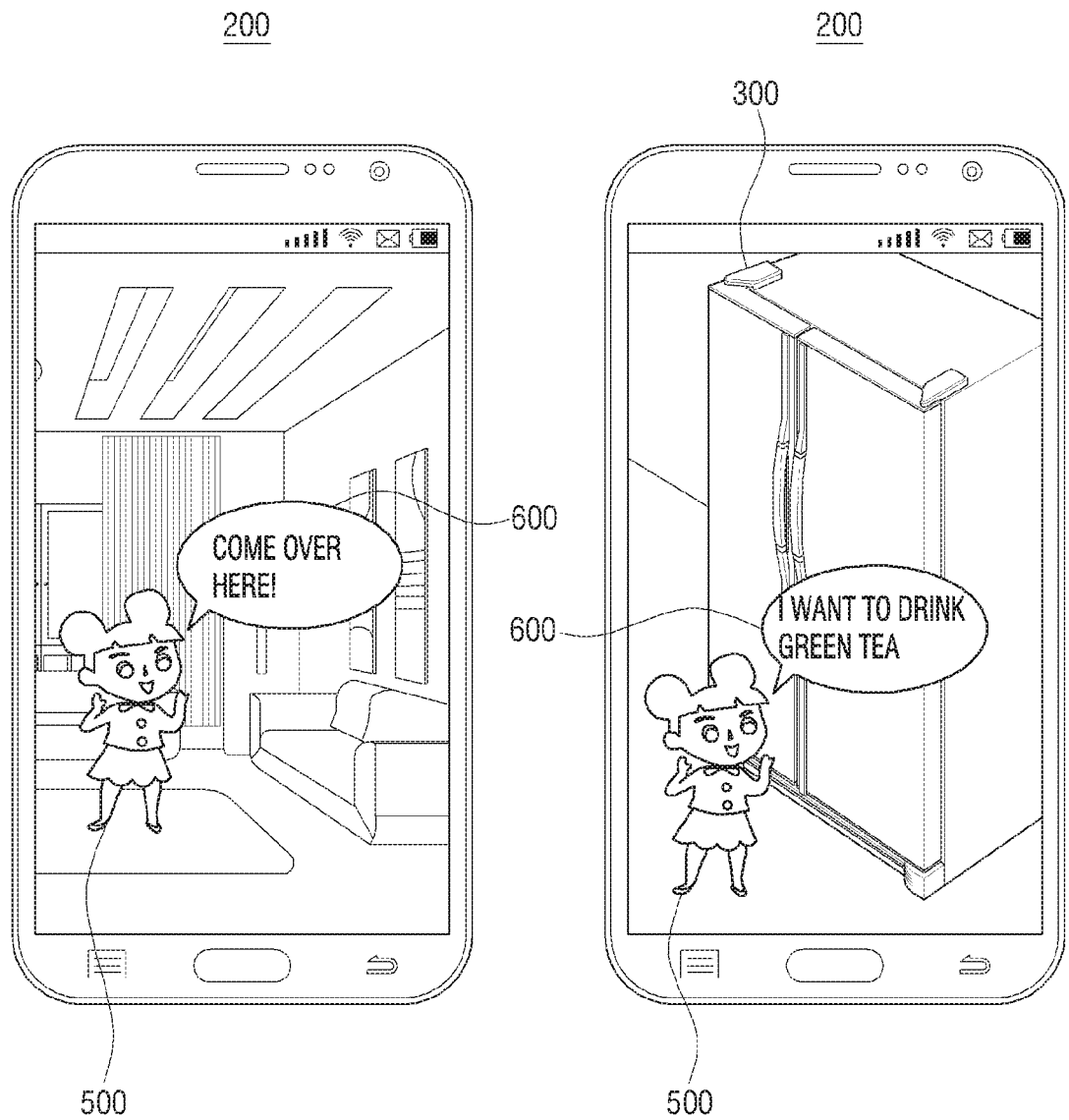
FIGS. 9A and 9B are diagrams for describing guide information to be displayed by compositing an avatar of a user to an image photographed through a camera according to an embodiment of the present disclosure.

FIGS. 9A and 9B are diagrams for describing guide information to be displayed by compositing an avatar of a user to an image photographed through a camera according to an embodiment of the present disclosure.

As illustrated in FIGS. 9A and 9B, the guide information in the form of guiding the behavior of the user may be provided using an augmented reality technology.

Specifically, the user terminal device 200 may transmit an image frame generated by capturing the image and the location information of the user terminal device 200 to the server 400, and may display an AR content for the image provided from the server 400 on the display together with a real time image.

As illustrated in FIGS. 9A and 9B, the AR content may be guide information including an avatar that guides the user to a place where the electronic device 300 is located and suggests a current necessary behavior for the user. To this end, the server 400 may receive the location information on the electronic device 300 from the user terminal device 200 or the electronic device 300, or may use the pre-stored location information of the electronic device 300, as described above.

Accordingly, there is an effect that the user may receive the guide information including the information associated with the function of the electronic device 300 through the user terminal device 200, even in case that the electronic device 300 does not include the display.

Figures 10A, 10B:
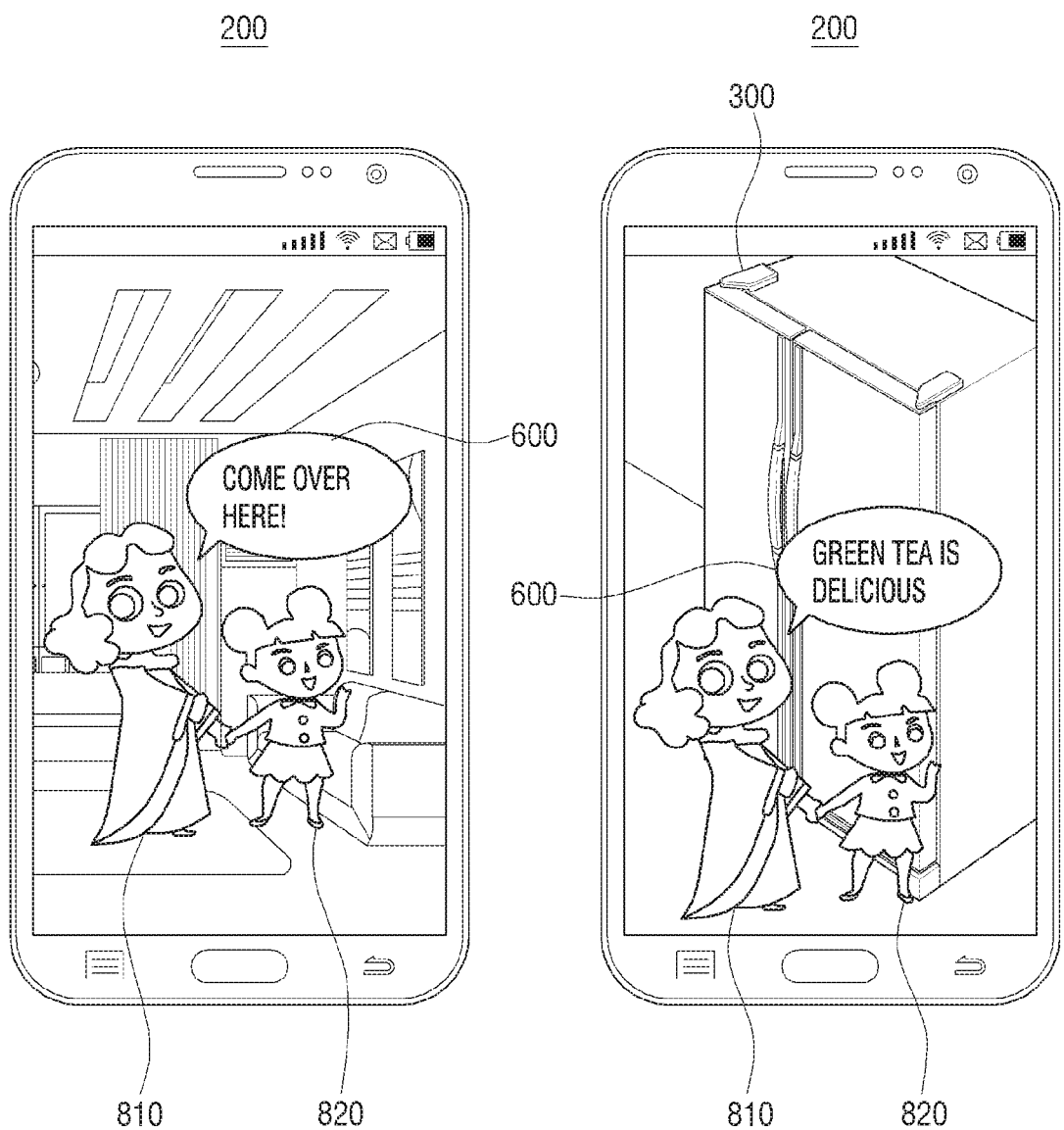
FIGS. 10A and 10B are diagrams for describing guide information in which an avatar of another user is displayed together with an avatar of a user according to an embodiment of the present disclosure.

FIGS. 10A and 10B are diagrams for describing guide information in which an avatar of the other user is displayed together with an avatar of a user according to an embodiment of the present disclosure.

First, the server 400 may be pre-stored with the access to health care information of an avatar 820 of the user by the other user. For example, the server 400 may be pre-stored with the access to health care information of a second user by a first user.

In this case, if a user terminal device of the other user and the user terminal device 200 are located within a predetermined distance range, an avatar 810 of the user terminal device of the other user and an avatar 820 of the user terminal device 200 may be displayed on the user terminal device 200 together with the real time image captured by the camera by the user terminal device 200, as illustrated in FIGS. 10A and 10B. Here, the guide information in the form of guiding the behavior of the user using the avatar 810 of the other user may be provided using an augmented reality technology.

Accordingly, when the user corresponding to the avatar 820 is a child, a guardian may more efficiently control a behavior of a guarded person in that the guide information may be provided through the guardian avatar 810.

Figure 11:
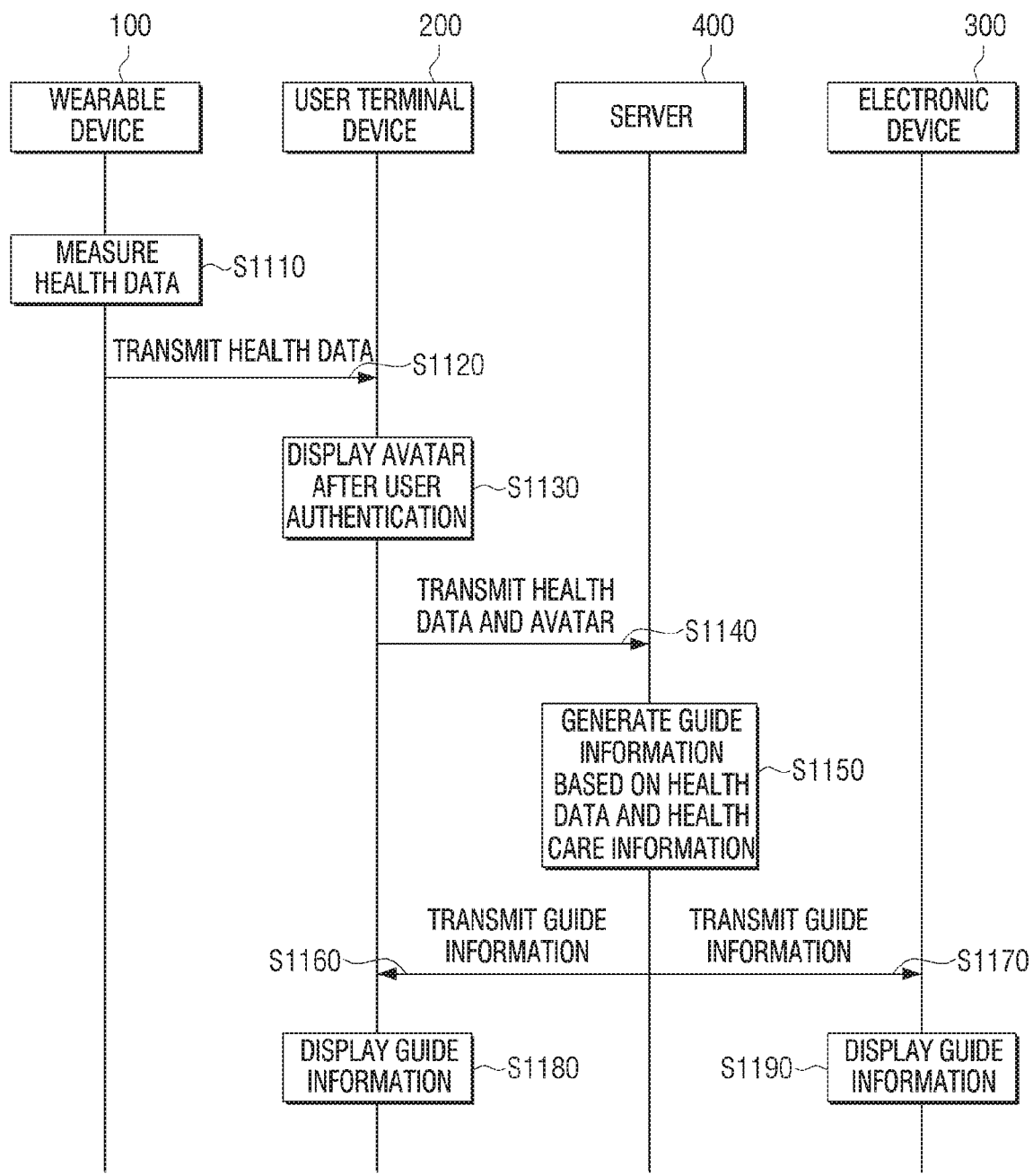
FIG. 11 is a flowchart for describing a guide information providing system according to an embodiment of the disclosure.

FIG. 11 is a flowchart for describing a guide information providing system according to an embodiment of the disclosure.

First, the wearable device 100 may be worn on a body of the user and measure the health data (S1110). In addition, the measured health data may be transmitted to the user terminal device 200 through communication with the user terminal device 200 (S1120). Here, the health data may be blood glucose, calories, sleeping information, and the like of the user.

In addition, if a user authentication is completed, the user terminal device 200 may generate an avatar corresponding to the user (S1130), and may transmit the generated avatar to the server 400 together with the health data received from the wearable device 100.

Thereafter, the server 400 may obtain health care information corresponding to the avatar of the user among the health care information corresponding to pre-stored one or more avatars. In addition, the server 400 may generate guide information for guiding the behavior of the user based on the obtained health care information and the received health data (S1150).

Here, the generated guide information may be transmitted to at least one of the user terminal device 200 or the electronic device 300 (S1160, S1170). Thereafter, the user terminal device 200 or the electronic device 300 may display the received guide information to guide a specific behavior of the user (S1180, S1190).

Figure 12:
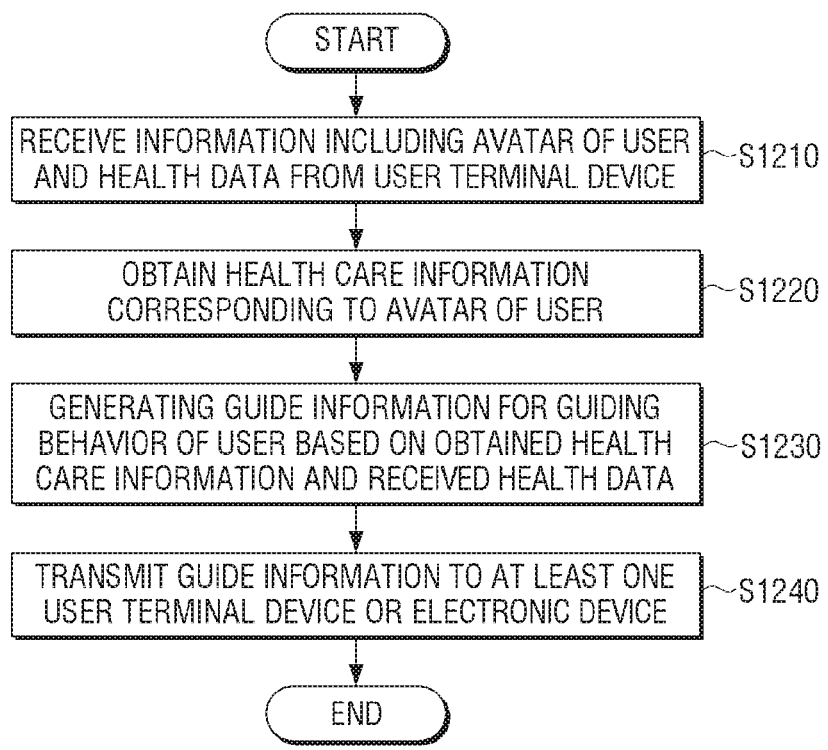
FIG. 12 is a flowchart for describing a method for providing guide information according to an embodiment of the present disclosure.

FIG. 12 is a flowchart for describing a method for providing guide information according to an embodiment of the present disclosure.

First, the server 400 may receive information including the avatar of the user and the health data from the user terminal device 200 (S1210). In addition, the server 400 may obtain health care information corresponding to the avatar of the user among the health care information corresponding to pre-stored one or more avatars (S1220). Thereafter, the processor 400 may generate guide information for guiding the behavior of the user based on the obtained health care information and the received health data (S1230), and may transmit the generated guide information to at least one of the user terminal device or the electronic device (S1240).

According to the diverse embodiments of the disclosure described above, because the guide information in the form of guiding the behavior of the user may be provided, the user may more effectively manage the health.

In particular, by enabling the health data generated in the wearable device 100 to be stored and processed in the server 300 as well as the user terminal device 200, it is possible not only to accumulate personal data for a long period of time, but also to recommend guide information matched to a situation in real time according to a user activity radius and the electronic device 300 based on accumulated data rather than a passive concept of simple data accumulation.

In addition, by using the avatar of the user reflecting personal health information as personal authentication and a personal data classification marker in the server 400, there is an effect that the continuity of data between the devices may be ensured along with the exchange and storage of data between the devices in accordance with the movement of the avatar. In addition, through avatar generation and upbringing behaviors, the user may also expect to have an interest in the health care itself. Meanwhile, the method for controlling the server, the user terminal device, and the electronic device according to the above-described diverse embodiments may be implemented as a program and stored in various recording media. That is, a computer program which is processed by various processors and is capable of executing the above-described various control methods may be used in a state being stored in the recording medium.

As an example, a non-transitory computer readable medium in which a program performing receiving information including an avatar of a user and health data, obtaining health care information corresponding to the avatar, and generating guide information based on the health care information and the health data is stored may be provided.

The non-transitory computer readable medium is not a medium that stores data for a short time such as a register, a cache, a memory, or the like, but means a machine readable medium that semi-permanently stores data. Specifically, various applications or programs described above may be stored and provided in the non-transitory computer readable medium such as a compact disk (CD), a digital versatile disk (DVD), a hard disk, a Blu-ray disk, a universal serial bus (USB), a memory card, a read only memory (ROM), or the like.

Although the embodiments of the disclosure have been illustrated and described hereinabove, the disclosure is not limited to the specific embodiment described above, but may be variously modified by those skilled in the art to which the disclosure pertains without departing from the scope and spirit of the disclosure as claimed in the claims. These modifications should also be understood to fall within the technical spirit and scope of the disclosure.

What is claimed is:

1. A server comprising:
   a communication interface configured to communicate with a plurality of user terminal devices and an electronic device;
   a storage configured to store health care information corresponding to a plurality of user avatars; and
   a processor configured to:
      control the communication interface to receive information including a plurality of user avatars and health data from the plurality of user terminal devices,
      obtain the health care information corresponding to the plurality of user avatars, from the storage,
      based on first location information about a location of a user terminal device among the plurality of user terminal devices and second location information about a location of the electronic device, identify whether the user terminal device accesses a location of the electronic device,
      based on first location information about a locations of the user terminal device and third location information about a location of another user terminal device, identify whether a distance between the user terminal device and the other user terminal device is less than predetermined value,
      based on determining that the user terminal accesses the location of the electronic device and the distance between the user terminal device and the other user terminal device being less than the predetermined value, identify guide information for guiding a user behavior based on a function of the electronic device and at least one of the obtained health care information, the received health data, or the received information including another user avatar of the other user terminal device, wherein the guide information comprises information in which the avatar guides the user behavior, control the communication interface to transmit the identified guide information to at least one of the plurality of user terminal devices or the electronic device, based on receiving user behavior information from the electronic device after the transmitting of the guide information, update the health care information stored in the storage based on the received user behavior information, change a state of the avatar based on the updated health care information, and control the communication interface to transmit the changed avatar to the at least one of the plurality of user terminal devices or the electronic device, wherein the processor is configured to change a motion of the avatar in real time based on the health data, and control the communication interface to transmit the changed motion of the avatar to the at least one of the plurality of user terminal devices or the electronic device.

2. A method for providing guide information to at least one of a plurality of user terminal devices or an electronic device, the method comprising:

receiving information including a plurality of user avatars and health data from the plurality of user terminal devices;

obtaining health care information corresponding to the plurality of user avatars;

based on first location information about a location of a user terminal device among the plurality of user terminal devices and second location information about a location of the electronic device, determining whether the user terminal device accesses a location of the electronic device;

based on the first location information about the location of the user terminal device and third location information about a location of another user terminal device, identifying whether a distance between the user terminal device and the other user terminal device being less than a predetermined value;

based on determining that the user terminal device accesses the location of the electronic device and the distance between the user terminal device and the other user terminal device being less than the predetermined value, identifying guide information for guiding a user behavior based on a function of the electronic device and at least one of the obtained health care information, the received health data, or the received information including another user avatar of the user terminal device, wherein the guide information comprises information in which the avatar guides the user behavior;

transmitting the identified guide information to at least one of the plurality of user terminal devices or the electronic device;

based on receiving user behavior information from the electronic device, updated the health care information based on the received user behavior information;

changing a state of the avatar based on the updated care information; and transmitting the changed avatar to the at least one of the plurality of the user terminal devices or the electronic device;

wherein the method further comprises;

changing a motion of the avatar in real time based on the health data; and transmitting the changed motion of the avatar to the at least one of the plurality of user terminal device or the electronic device.

* * * * *